United States Patent [19]
Weber et al.

[11] Patent Number: 6,117,098
[45] Date of Patent: Sep. 12, 2000

[54] ANKLE BRACE

[75] Inventors: James J. Weber, Santa Barbara; John P. Hely, Oxnard, both of Calif.

[73] Assignee: Weber Orthopedic, Inc., Santa Paula, Calif.

[21] Appl. No.: 09/273,946

[22] Filed: Mar. 22, 1999

[51] Int. Cl.$^7$ ................................................. A61F 13/00
[52] U.S. Cl. ............................................. 602/27; 602/65
[58] Field of Search ............................... 602/23, 27–29, 602/60, 65; 128/882

[56] References Cited

U.S. PATENT DOCUMENTS

| | | |
|---|---|---|
| 3,073,305 | 1/1963 | Biggs, Jr. et al. . |
| 3,506,000 | 4/1970 | Baker . |
| 3,674,023 | 7/1972 | Mann .................................... 602/27 |
| 4,280,488 | 7/1981 | Polsky et al. . |
| 4,313,433 | 2/1982 | Cramer . |
| 4,323,058 | 4/1982 | Detty . |
| 4,367,733 | 1/1983 | Stromgren . |
| 4,573,482 | 3/1986 | Williams, Jr. . |
| 4,597,395 | 7/1986 | Barlow et al. . |
| 4,621,648 | 11/1986 | Ivany . |
| 4,729,370 | 3/1988 | Kallassy . |
| 4,844,058 | 7/1989 | Vogelback . |
| 4,878,504 | 11/1989 | Nelson . |
| 5,007,415 | 4/1991 | Marion ................................ 602/16 X |
| 5,050,620 | 9/1991 | Cooper . |
| 5,067,486 | 11/1991 | Hely . |
| 5,151,081 | 9/1992 | Williams . |
| 5,217,431 | 6/1993 | Toronto et al. . |
| 5,226,875 | 7/1993 | Johnson .................................... 602/27 |
| 5,330,419 | 7/1994 | Toronto et al. . |
| 5,472,414 | 12/1995 | Detty . |
| 5,620,413 | 4/1997 | Olson . |
| 5,676,641 | 10/1997 | Arensdorf et al. . |
| 5,695,452 | 12/1997 | Grim et al. ........................... 602/19 X |
| 5,795,316 | 8/1998 | Gaylord . |
| 5,822,887 | 10/1998 | Turner . |
| 5,891,073 | 4/1999 | Deimendjian et al. ................ 602/27 |

FOREIGN PATENT DOCUMENTS

| | | |
|---|---|---|
| 3416253 | 7/1985 | Germany . |

*Primary Examiner*—Danton D. DeMille
*Assistant Examiner*—Denise Pothier
*Attorney, Agent, or Firm*—William W. Haefliger

[57] ABSTRACT

In ankle brace apparatus, the combination comprises a foot and ankle holder having a foot portion, and having an upper ankle portion with opposite first and second sides; support strap structure operatively connected to a holder to extend under foot portion and then to extend generally upwardly and rearwardly for retention to those opposite sides at retention zones; and retention flaps connected to the holder and extending forwardly to overlap support strap structure at retention zones, the retention flaps spaced apart to provide freely adjustable and conforming cushioning at the rear of the holder.

20 Claims, 4 Drawing Sheets

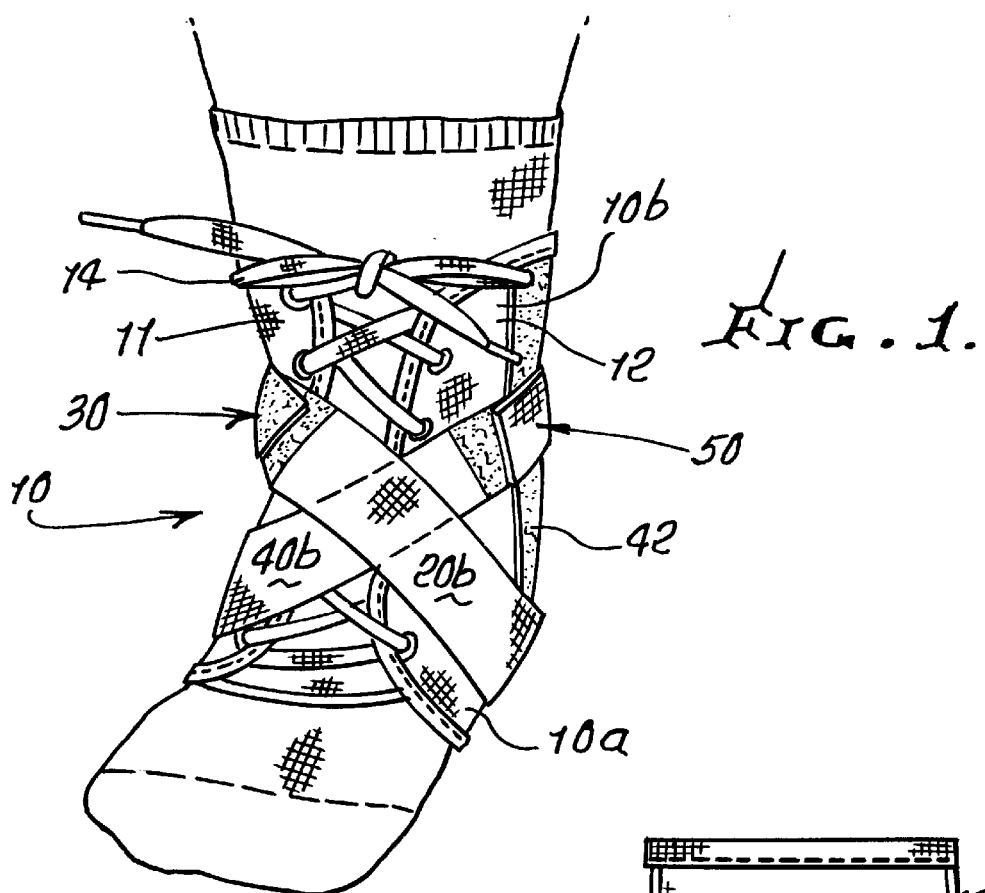
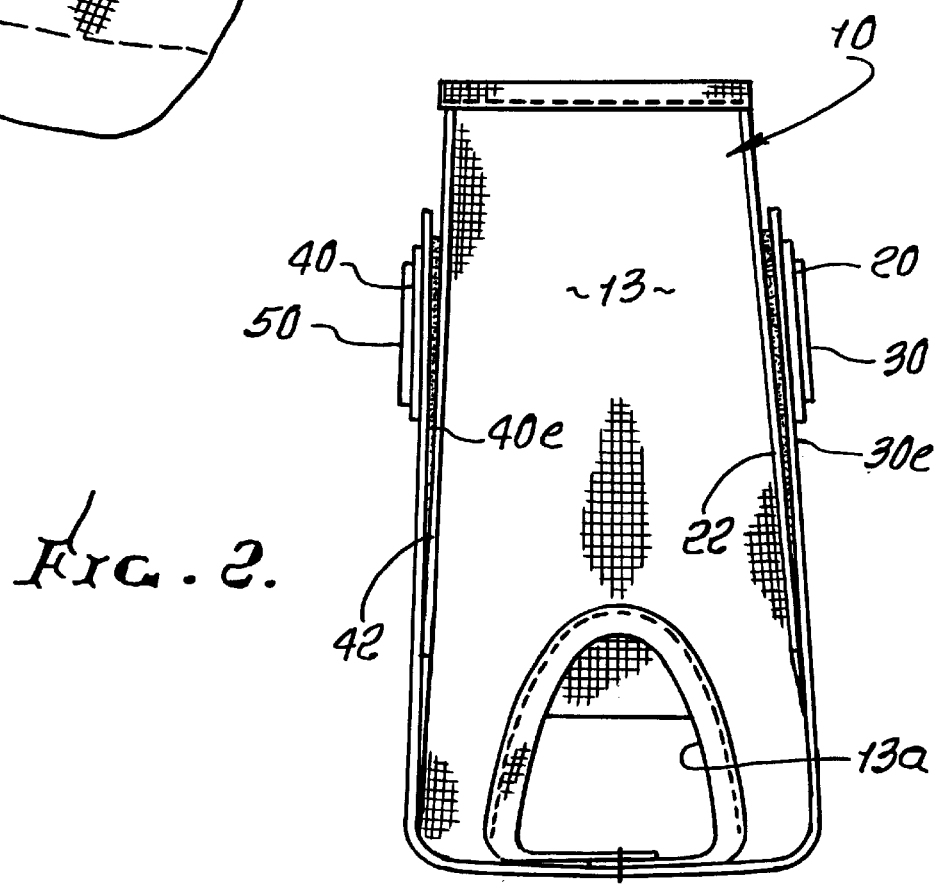

ANKLE BRACE

BACKGROUND OF THE INVENTION

This invention relates generally to ankle braces, and more particularly to improvements in such braces enabling ease and rapidity of application to the wearer's ankle, as well as enhanced ankle stability.

Injuries to ankles such as sprains frequently require the application of ankle braces, which must be repeatedly applied and removed at frequent intervals. Accordingly, ease and rapidity of application and removal are essential. There is need for improvements in ankle braces enabling such ease and rapidity of brace application and removal, as well as providing for enhanced ankle stability when applied.

SUMMARY OF THE INVENTION

It is a major object of the invention to provide an improved ankle brace meeting the above need. Basically, the ankle brace apparatus embodying the invention comprises:

a) a foot and ankle holder having a foot portion, and having an upper ankle portion with opposite first and second sides, b) support strap structure operatively connected to the holder to extend under the foot portion and then to extend generally upwardly and rearwardly for retention to holder opposite sides at retention zones, c) and retention strap structure in the form of a first flap connected to the holder upper ankle portion to extend forwardly to overlap the support strap structure at a retention zone.

As will appear stabilized and simplified support at ankle opposite sides is paramount, strap support at the rear of the holder not then being required, and the rear of the holder being left freely adjustable and strap free to provide conforming cushioning.

A further object is to provide support strap structure having end portions overlapping the retention zones, and the retention flap or flaps forwardly overlapping end portions of the support strap structure. As will be seen, two of such support strap end portions and a flap form a sandwich configuration, at each side of the holder ankle portion.

Another object is to provide a stiffener retained in at least one of the sandwich configurations, and an upright stiffener may be provided at each of the sandwich configurations at opposite sides of the ankle.

An additional object is to provide for hook and pile attachment of the support strap structure to at least one of the ankle holder opposite sides, and preferably at both such opposite sides.

A yet further object is to provide hook and pile attachment of the retention strap structure to at least one of the support strap structures opposite ends, and typically to each of the support strap structure opposite ends.

A yet additional object is to provide two support straps and two of said flaps, each support strap having an end with hinge attachment to a holder, and each of the flaps having hinge attachment to said holder upper angle portion, the hinge attachment of each flap being proximate the hinge attachment of support strap, at one side or sides of the holder.

All of such hinge connections, which may be sewn, are preferably spaced from rearward extent of said holder whereby said rearward extent provides a freely adjustable and strap free conforming cushion at the rear of the holder.

These and other objects and advantages of the invention, as well as the details of an illustrative embodiment, will be more fully understood from the following specification and drawings, in which:

DRAWING DESCRIPTION

FIG. 1 is a frontal elevation, in perspective showing apparatus embodying one preferred form of the invention, as applied to a wearer's ankle, with all straps attached or anchored, in position;

FIG. 2 is an enlarged rear elevation of the apparatus of FIG. 1;

DETAILED DESCRIPTION

Figure 3:
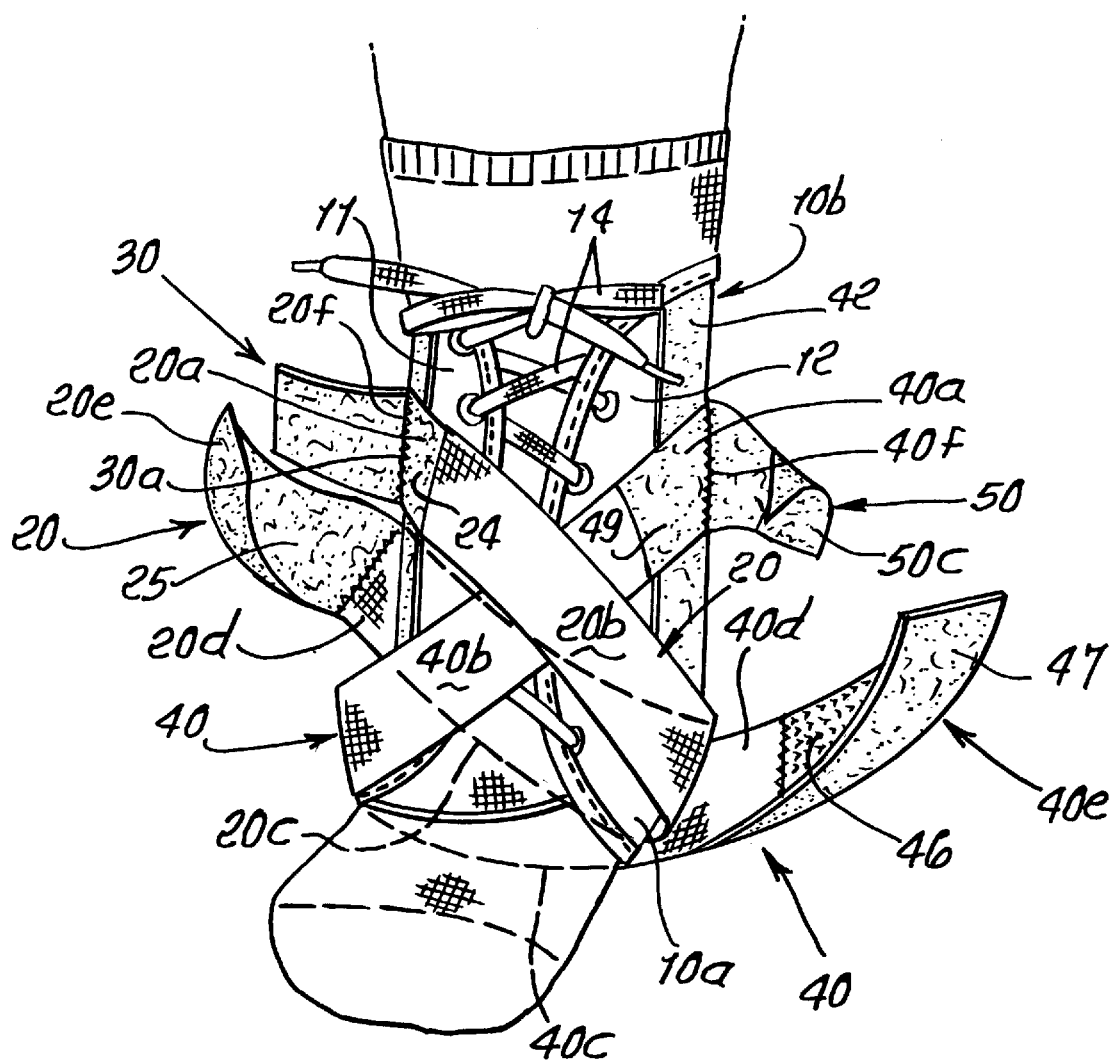
FIG. 3 is a view like FIG. 1, showing all straps and flaps in loosened condition.
Figure 5:
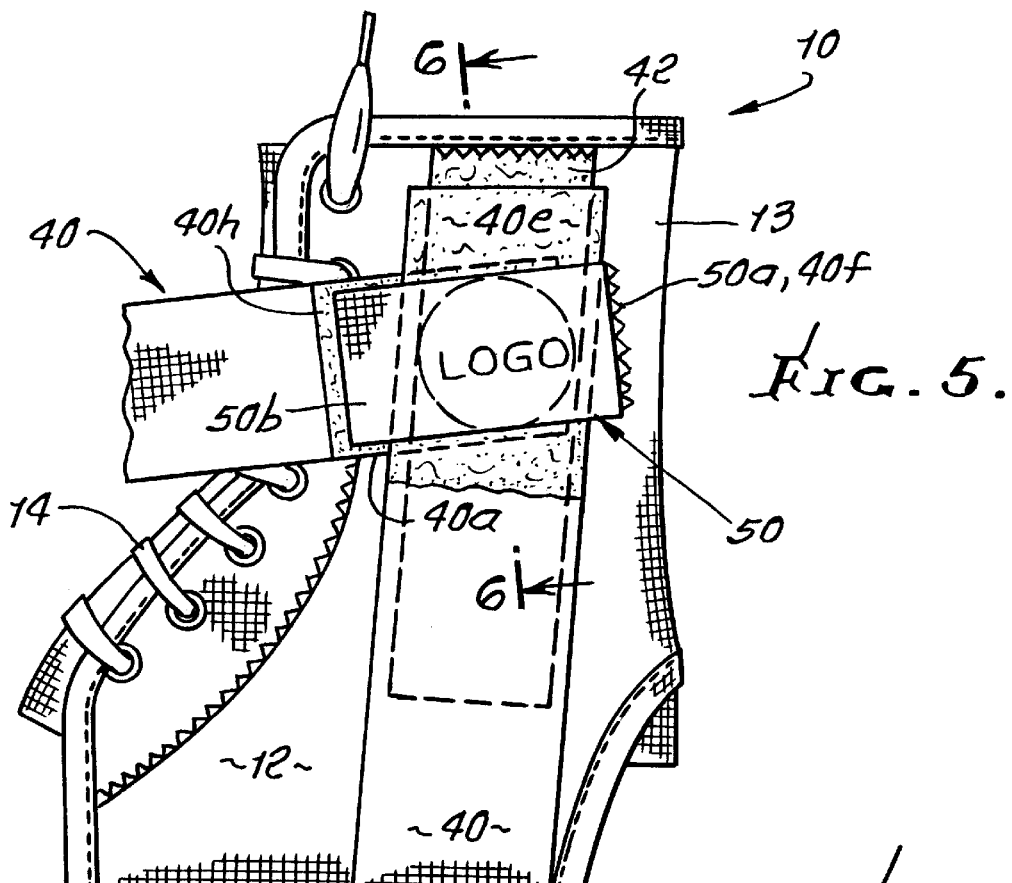
FIG. 5 is a right side elevation, showing strap ends and a flap interconnected to provide a sandwich configuration.

In the preferred embodiment FIGS. 1, 3 and 5, a holder in the form of a boot 10 for the foot and ankle of a wearer is shown to have a lower foot portion 10a and an upper ankle portion 10b. Opposite panel sides of the portion 10b are indicated at 11 and 12. Side 11 is at the outer side of the ankle, and side 12 is at the inner side of the ankle. The rear side of the holder is seen at 13, and a lower cut-out 13a is formed in 13 to receive the heel of the wearer. Laces 14 to draw sides 11 and 12 toward one another are seen at the front of the holder or boot. The holder may consist of non-stretchable Nylon fabric, which is durable and flexible.

Support strap structure is provided, and is operatively connected to the holder 10 to extend under foot portion 10a and then to extend generally upwardly for retention to opposite sides 11 and 12, at retention zones. See for example FIG. 3 showing strap 20 having one end portion 20a hinge connected at 20f as by stitching to the holder side 11, above ankle level, the strap then extending forwardly and downwardly at 20b across the laces, then downwardly under the lower foot portion 10a of the holder at 20c, then back upwardly at 20d at the side of the ankle for operative connection of strap opposite end portion 20e to the holder, typically in overlying relation to end portion 20a. The operative connection may advantageously consist of inner side hook and pile material 25 connected to outer pile or hook material 24 on 20a.

Retention flap structure in the form of a first flap is also provided. It is connected to the holder ankle portion at a side location and extends forwardly to overlap the support strap structure at a retention zone or zones. For example, the retention flap forwardly overlaps end portions of the support strap structure.

Figure 6:
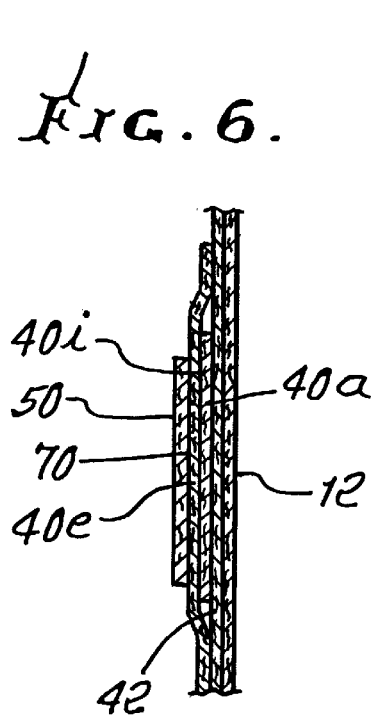
FIG. 6 is a schematic edge view showing strap and flap layers, in the sandwich configuration.

As shown in the Figures, including FIGS. 1 and 6, retention flap 30 is connected at one end, as by stitching at 30a, to the holder side 11, and extends forwardly as a free flap to be manipulated to extend closely over the sandwiched strap ends 20a and 20e, for holding them in superimposed position and for protecting them from dislodgement, as by accidental impact with objects such as furniture. Stitching 30a and 20f may be the same.

Similarly, a second support strap 40 is provided to have one end portion 40a hinge connected at 40f to the holder side 12, above ankle level, the strap then extending downwardly at 40*b* across the laces, under strap extent 20*b* and then downwardly and under the lower foot portion of the holder at 40*c*, crossing 20*c*, and then back upwardly at 40*d* at the opposite side of the ankle, for operative connection of strap 40 opposite end portion 40*e* to the holder, typically in overlying relation to end portion 40*a*. Such operative connection may advantageously consist of inner side hook and pile material at 46 connected to outer pile or hook material 49 on 40*a*.

Retention flap 50 is connected at its rearward end as by vertical stitching at 50*a*, to the holder side 12, and extends forwardly, as a free flap, to be manipulated to extend closely over the sandwiched strap ends 40*a* and 40*e*, for holding them in superimposed interconnected positions, and for protecting them from dislodgement, as by inadvertent contact with objects such as furniture. Note inner hook or pile material 50*c* on 50 connected to outer pile or hook material 47 on strap end 40*e*.

Figure 4:
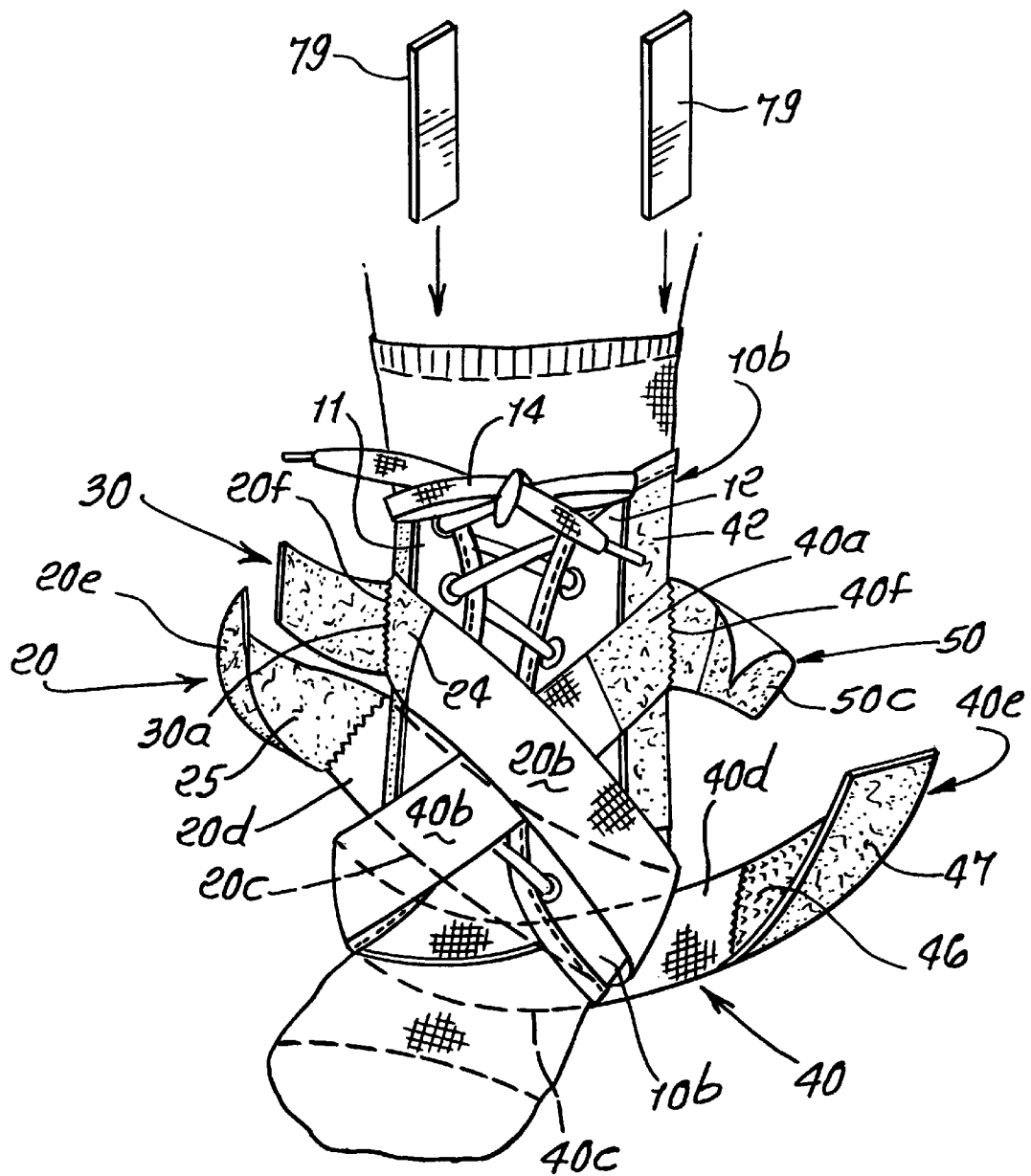
FIG. 4 is a view like FIG. 3, showing provision for stiffeners.
Figure 7:
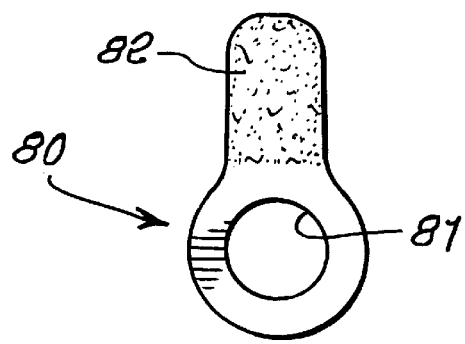
FIG. 7 is a frontal view of a modified stiffener.
Figure 8:
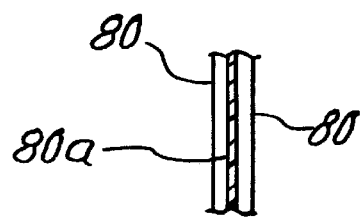
FIG. 8 is a top end view of stacked multiple stiffeners.

FIG. 4 shows optional, but recommended, provision of vertically elongated stiffeners 79 in the form of narrow, thin, rigid plates carrying hook or pile fabric at their opposite sides. Such stiffeners are easily applied between strap ends 20*a* and 20*e* (having hook or pile layers thereon) and between strap ends 40*a* and 40*e* (having hook or pile layers thereon). Accordingly, the stiffeners are held in protectively sandwiched position in the assemblies, and enhance ankle stability. The stiffener plates may consist of molded plastic material. FIG. 7 shows a modified stiffener 80 having a through opening 81 to register with the sideward jutting ankle bone of the wearer so as to comfortably fit in position. Retention hook or pile area is shown at 82 on upper extent of 80. Multiple such stiffeners 80 may be stacked together as seen in FIG. 8, and connected by hook and pile zones as at 80*a*, to selectively and increasingly stiffen ankle region. The stiffeners may be located between strap end portions 20*a* and 40*a*, and the holder sides. The stiffeners can be made of plastic material that conforms to the shape of the ankle surface.

Referring to use of the support strap 40, it is wrapped under the foot, as previously described, and the user then brings end 40*e* upwardly to overlay and connect (at hook and pile interface 40*f*) to the hinged strap end 40*a*. Strap end 40*e* may attach to hook or pile vertical extent 42 affixed to boot side 12, for additional support, as seen in FIG. 5. And, likewise, strap end 20*e* may attach to vertical hook and pile material 22 affixed to boot side 11, for additional support, as seen in FIGS. 3 and 4.

A strap retention zone is thereby defined, by the overlay structures, and underfoot tightness or looseness is adjusted by the vertical positioning of strap end 40*e*.

Next, the user brings the retention flap 50 into overlying relation to the overlying strap ends 40*a* and 40*e*, and pushes the flap into removable connection to strap end 40*e*, at hook and pile interface 70 seen in FIG. 6. The interface between 40*a* and 40*e* appears at 40*i*. The forwardmost extent 50*b* of flap 50 can then be removably connected to strap 40 at hook and pile zone 40*h* immediately forwardly of end 40*a*, as seen in FIG. 5.

An identifying label (LOGO) in FIG. 5 is shown as attached to the outer side of flap 50.

By hinge connecting each of straps 20 and 40 to the holder at sewn hinge locations that are spaced apart; and by hinge connecting each of the flaps 30 and 50 to the holder at sewn hinge locations that are spaced apart, the rear of the holder is left free of any overlying holder or flap material, so that it can conformingly, thereby to provide a cushion between uppermost and lowermost extents of the rear of the holder, to comfortably adjust to the wearer's foot at the thereby unconstrained Achilles tendon area, and at the same time, the ankle brace performs its ankle bracing functions. Note that neither the straps nor the flaps overlie the Achilles tendon area at the rear of the holder.

Multiple support straps as at 20 and 40 can be provided to overlie one another, such as a pair or more of overlying like straps 20, and/or a pair or more of overlying like straps 40, to increase the strength and/or stiffeners of the ankle brace composite, at the side or sides of the ankle.

We claim:

1. In ankle brace apparatus, the combination comprising
   a) a foot and ankle holder having a foot portion, and having an upper ankle portion with opposite first and second sides,
   b) support strap structure operatively connected to said holder to extend under said foot portion and then to extend generally upwardly and rearwardly for removable retention to at least one of said opposite sides at a retention zone,
   c) and retention strap structure having a first flap connected to said holder upper ankle portion at a location proximate said strap retention zone at one of the holder opposite sides, and extending forwardly to overlap said support strap structure at said retention zone and to removably connect to said support strap structure forwardly of said retention zone,
   d) said support strap structure including two support straps wrapped in opposite directions under said holder foot portion, said support straps having first end portions which have hinge attachments to said holder upper ankle portion opposite first and second sides, respectively, said hinge attachments spaced apart to provide freely exposed strap free cushioning at the rear of said holder,
   e) said rear of the holder being free of any overlying strap structure between the uppermost and lowermost extents thereof, whereby said cushioning is unrestricted by any strap structure, and said rear of the holder provides a strap free conforming cushion.

2. The combination of claim 1 wherein said support strap structure has a second end portion overlapping the first end portion beneath said flap.

3. The combination of claim 2 wherein said end portions and said flap form a sandwich configuration, at said at least one of said opposite sides.

4. The combination of claim 3 including a stiffener retained in said sandwich configuration.

5. The combination of claim 4 wherein said stiffener has a through opening positioned for registration with the wearer's ankle.

6. The combination of claim 3 including multiple stiffeners retained in said sandwich configuration.

7. The combination of claim 6 wherein said multiple stiffeners extend adjacent one another, in stacked relation.

8. The combination of claim 7 wherein said stiffeners have through openings positioned for registration with the wearer's ankle protrusion.

9. The combination of claim 2 wherein said first flap has hook and pile attachment to one of the second end portions.

10. The combination of claim 1 wherein said retention strap structure includes a second flap connected to said holder upper ankle portion at the other of said holder sides, and extending forwardly to removably connect to support strap structure forwardly of a second retention zone.

11. The combination of claim 10 including upright stiffeners retained beneath said first and second flaps.

12. The combination of claim 11 wherein, one stiffener is located under said first and second end portions of one of said support straps, and the other stiffener is located under said first and second end portions of the other of said support straps.

13. The combination of claim 10 wherein said support strap structure has hook and pile attachment to each of said ankle holder opposite sides.

14. The combination of claim 10 wherein one of said flaps has hook and pile attachment to a second end portion of one of the support strap structure, and the other of said flaps has hook and pile attachment a second end portion of to the other of the support strap structure.

15. The combination of claim 1 wherein said support strap structure has hook and pile attachment to at least one of said ankle holder opposite sides.

16. The combination of claim 1 wherein there are two support straps and two of said flaps, each support strap having an end with hinge attachment to said holder, and each of the flaps having hinge attachment to said holder upper ankle portion, the hinge attachment of each flap being proximate the hinge attachment of a support strap.

17. The combination of claim 16 including at least one additional support strap overlying at least one of said two support straps, and connected thereto.

18. The combination of claim 17 wherein at least one of said flaps overlies said additional support strap, to provide a tight, interlocked multiple support strap and flap assembly.

19. The combination of claim 17 wherein each of said flaps overlies one additional support strap, to provide a tight, interlocked multiple support strap and flap assembly at both sides of the holder.

20. The combination of claim 1 wherein said spaced apart hinge attachments extend generally vertically.

\* \* \* \* \*